United States Patent [19]

Curtis

[11] Patent Number: 4,602,097
[45] Date of Patent: Jul. 22, 1986

[54] WATER SOLUBLE PHOTOINITIATOR BENZOPHENONE AND THIOXANTHENONE ETHOXY-ETHER DERIVATIVES

[75] Inventor: John R. Curtis, Lawrenceville, N.J.

[73] Assignee: Ulano Corporation, Brooklyn, N.Y.

[21] Appl. No.: 619,604

[22] Filed: Jun. 11, 1984

[51] Int. Cl.⁴ ............... C07D 335/16; C07D 409/12; C07D 49/786
[52] U.S. Cl. ..................................... 549/27; 562/460; 564/82; 564/86; 564/88; 564/89; 564/163; 564/166; 564/169; 564/171; 564/306; 564/322; 568/42; 568/43; 568/309; 568/332
[58] Field of Search ............... 548/444; 549/27, 223; 568/309, 326, 332, 335, 425, 42, 43; 562/460; 564/82, 86, 88, 89, 163, 166, 169, 171, 306, 322

[56] References Cited

FOREIGN PATENT DOCUMENTS

| | | | |
|---|---|---|---|
| 1307995 | 2/1973 | United Kingdom | 549/27 |
| 1366304 | 9/1974 | United Kingdom | 549/27 |
| 2108487 | 5/1983 | United Kingdom | 549/27 |
| 2108979 | 5/1983 | United Kingdom | 549/27 |

Primary Examiner—Henry R. Jiles
Assistant Examiner—J. G. Mullins
Attorney, Agent, or Firm—Charles E. Baxley

[57] ABSTRACT

Photoinitiators of the formula

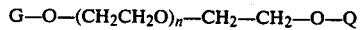

$$G-O-(CH_2CH_2O)_n-CH_2-CH_2-O-Q$$

wherein G is a photoinitiator moiety, R is hydrogen or lower alkyl, n has a value of at least 10, and Q is G or a lower alkyl are soluble in water and common organic solvents and are useful in polymerization systems employed in coatings used in screen printing.

16 Claims, No Drawings

WATER SOLUBLE PHOTOINITIATOR BENZOPHENONE AND THIOXANTHENONE ETHOXY-ETHER DERIVATIVES

This invention relates to photoinitiators which, when admixed with suitable unsaturated photopolymerizable compounds, can, when irradiated with UV light, produce free radicals which initiate photopolymerization of said polymerizable compounds. It particularly relates to photoiniators which are soluble both in water and the common organic solvents.

BACKGROUND OF THE INVENTION

The photopolymerization of unsaturated compounds can be substantially accelerated by a wide variety of initiators, including such compounds as acetophenone, propiophenone, benzophenone, xanthone, thioxanthone, fluorenone, benzaldehyde, anthraquinone, carbazole, thioindigoid dyes, various derivatives of these compounds and certain metalic salts such as ferric salts of carboxylic acids. Most of these initiators are water-insoluble and are not suitable for use in water-based systems. When a water-insoluble initiator is used in a water-based system it is necessary that the initiatior be dissolved in a non-aqueous solvent and dispersed with photopolymerizable material into the aqueous phase to form an emulsion. If the photopolymerizable material present is water-soluble, then the initiator is in a separate phase and cannot work very effectively to bring about photopolymerization on exposure to actinic light. If, on the other hand, the unsaturated photopolymerizable compounds are in the same (solvent) phase as the initiator, then although photopolymerization can take place more efficiently, the ability of the photopolymerized material to subsequently insolubilize the ingredients of the aqueous phase and in particular the protective colloid which is normally present is less effective.

In order to produce the most effective insolubilization of the aqueous phase ingredients by photopolymerization of the unsaturated compounds, it is preferable for the photopolymerizable unsaturated compounds to be totally or substantially water-soluble and for the initiator also to be water-soluble. When the initiator and unsaturated photopolymerizable material are both fully, or substantially, in the same (aqueous) phase, then photopolymerization on exposure to UV light can proceed efficiently and the resulting insolubilisation of the aqueous layer ingredients is effective.

For a photoinitiator to work efficiently when exposed to actinic light through glass (as is normally the case when the exposure is carried out with a printing down frame in screen printing), it is highly desirable for it to absorb above 3250 Å. However, many simple water soluble photoinitiators do not absorb above this level. Moreover, is the solubilization of a photoinitiator is attempted by simple sulphonation or inclusion of a carboxy group, the presence of the carboxy or sulpho group on a main benzene ring of the initiator, whether directly attached or separated by a single methylene group, deactivates the molecule and makes it less efficient as a photoinitiator.

At present, the water-soluble photoinitiators used in commercial screen printing, as described in U.K. Pat. No. 2,108,979, are ferric salts of carboxylic acids (U.K. Pat. No. 1,307,995 and solubilized indigoid vat colors (U.K. Pat. Nos. 1,307,995 and 1,366,304).

The use of ferric salts of carboxylic acids requires the presence of hydrogen peroxide, which is at times undesirable.

The commonly used indigoid vat colors are thioindigoid dyes sold under the name "ANTHRASOL" by Farbwerke Hoechst. These are capable of photoinitiating the polymerization of unsaturated compounds on exposure to UV light. However, they suffer from the extremely serious drawback that, to remain active, the layer to be photopolymerized must contain moisture. This requires the inclusion of quite large quantities of humectant in the layer which, under conditions of high ambient temperature and humidity can cause reticulation and breakdown problems in the layer.

Another group of water-soluble photoinitiators, reported in U.K. Pat. No. 2,108,487, are thioxanthones of the formula

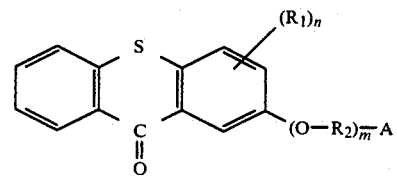

wherein $R_1$ is alkyl, alkoxy, alkylthio, halogeno, nitro, amino, alkyl-amino, di-alkyl-amino, hydroxy-alkyl-amino, alkanoylamino, benzoylamino, N-alkanoyl-N-benzoyl-amino, sulphonamido, or acetyl, $R_2$ is alkylene, A is —COOH, —SO$_3$H, —OSO$_3$H, or —O—CO—X—COOH (where X is such that HO—CO—X—COOH is a di- or tri-carboxylic acid of up to 9 carbon atoms), n is 0, 1 or 2 and m is 1 or 2, provided that when A is —COOH, m is 2, the aforesaid alkyl, alkoxy, alkanoyl, and alkylene residues containing up to 4 carbon atoms each, as the free acid or as a salt thereof. Especially valuable compounds are those in which $R_1$ is methyl, $R_2$ is ethylene, trimethylene, or tetramethylene, A is —SO$_3$H, n is 0, 1 or 2 and m is 1 or 2 as the free acid or as a water-soluble salt thereof.

These thioxanthones, like the other water-soluble photoinitiators are salts which are sensitive to changes in pH, and the salt forming groups interfere with the stability of dispersions of collods, e.g. gelatin, which may be present in the polymerization system, resulting in the breakup of the stable colloidal dispersions. Besides, the presence of calcium ions in water, as occurs in hard water, may result in the precipitation of the calcium salts of the photoinitiators, thereby removing them from the system.

DESCRIPTION OF THE INVENTION

It is an object of this invention to provide water-soluble photoinitiators for use in polymerization systems.

It is another object of this invention to provide water-soluble photoinitiators which are also soluble in the common organic solvents, e.g. methanol, ethanol, acetone, ethylacetate, benzene, and the like.

It is a further object of this invention to provide water-soluble photoinitiators which are non-ionic.

Other objects will appear from the description which follows. In accordance with this invention there are provided water-soluble photoinitiators of the formula:

G—O—(CH$_2$—CH$_2$—O)$_n$—CH$_2$—CH$_2$—O—Q wherein

G is a photoinitiator moiety, n has a value of at least 10, and

Q is either G or a lower alkyl having 1 to 4 carbon atoms, with the proviso that when Q is G, n has a value of at least 19.

G is the residue of any suitable organic photoinitiator such as acetophenone, propiophenone, benzophenone, xanthone, thioxanthone, fluorenone, benzaldehyde, anthraquinone, carbazole, and the like and various substituted derivatives of these compounds. Preferred residues are thioxanthones of the formula

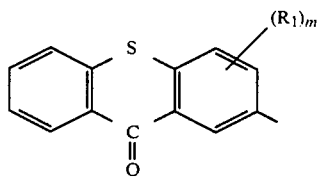

wherein $R_1$ is alkyl, alkoxy, alkylthio, halogeno, nitro, amino, alkylamino, dialkylamino, alkanoyl, alkanoylamino, benzoylamino, or sulfonamido, wherein the alkyl group in alkyl per se or in alkoxy, alkythio, alkylamino, dialkylamino, alkanoyl and alkanoylamino contains from 1 to 4 carbon atoms and may be straight chained or branched, and m is an integer from 0 to 2 inclusive. Where m is 0 $R_1$ becomes hydrogen.

When Q is G, n, as noted above should have a value of at least 19. Preferably, when Q is G, n is in the range from about 19 to about 75.

The compounds of this invention may be obtained by the reaction of a compound of the formula G—O—Na G is as defined above with a compound of the formula X—(CH$_2$—CH$_2$O)$_n$—CH$_2$—CH$_2$—Y wherein n is as defined above, X is a halogen, preferably chlorine, and Y is either X or lower alkoxy having 1 to 4 carbon atoms.

The G—O—Na intermediate is obtained by the reaction of P—OH with sodium hydroxide. Since the hydroxyl group in P—OH is attached to an aromatic ring it is phenolic in character and will readily react with the sodium hydroxide.

The dihalide can be readily obtained by the replacement of two hydroxyl groups in the compound HO—(CH$_2$—CH$_2$O)$_n$—CH$_2$CH$_2$OH wherein n is as defined above, with a suitable halogenating agent such as phosphorus tribromide, phosphorus trichloride, thionyl chloride, and the like. Thionyl chloride is preferred. The monohalide can be similarly prepared by the replacement of the hydroxyl in the compound HO—(CH$_2$—CH$_2$O)$_n$—CH$_2$CH$_2$OZ wherein n is as defined above and Z is a lower alkyl having from 1 to 4 carbon atoms.

The invention will become clearer from the Examples which follow. These Examples are given by way of illustration and are not to be regarded as limiting. Examples 1 to 7 illustrate the preparation of intermediates, Examples 8 to 15 the preparation of the novel water-soluble photoinitiators of this invention, and Examples 16 and 17 the use of these novel photoinitiators in polymerization systems.

EXAMPLE 1

Cl—(CH$_2$CH$_2$O)$_{21-22}$—CH$_2$CH$_2$Cl

| Polyethylene glycol (PEG 1000) n = 21–22 | 100 g |
|---|---|
| Thionyl chloride | 60 g |
| Dimethylformamide | 0.1 g |

The materials were mixed and stirred under reflux for about 4 hours. The excess thionyl chloride was distilled off under reduced pressure and the reaction mixture permitted to cool. Methanol was added to react with any remaining unreacted thionyl chloride and the methanol was then distilled off under reduced pressure. This distillation removed other remaining volatile materials, e.g. methyl chloride, sulfur dioxide, and dimethylformamide. The pale yellow oily residue solidified to a waxy cream white solid which could be used directly without further purification. Yield 103 g.

EXAMPLE 2

Cl—(CH$_2$CH$_2$O)$_{19}$CH$_2$CH$_2$Cl

| Polyethylene glycol (PEG 900) n = 19 | 100 g |
|---|---|
| Thionyl chloride | 60 g |
| Dimethylformamide | 0.1 g |

The procedure of Example 1 was repeated to give 100 g of the product.

EXAMPLE 3

Cl—(CH$_2$CH$_2$O)$_{75}$—CH$_2$CH$_2$Cl

| Polyethylene glycol (PEG 3350) n = 75 | 200 g |
|---|---|
| Thionyl chloride | 60 g |
| Dimethylformamide | 0.1 g |

The procedure of Example 1 was repeated to give 200 g of the product.

EXAMPLE 4

Cl—(CH$_2$CH$_2$O)$_{31-32}$—CH$_2$CH$_2$—Cl

| Polyethylene glycol (PEG 1450) n = 31–32 | 100 g |
|---|---|
| Thionyl chloride | 60 g |
| Dimethylformamide | 0.1 g |

The procedure of Example 1 was repeated to give 101 g of the product.

EXAMPLE 5

Cl—(CH$_2$CH$_2$O)$_{10-11}$—CH$_2$CH$_2$OCH$_3$

| Polyethylene glycol (PEG 550) monomethyl ether n = 10–11 | 100 g |
|---|---|
| Thionyl chloride | 60 g |

| | |
|---|---|
| -continued | |
| Dimethylformamide | 0.1 g |

The procedure of Example 1 was repeated to give 98 g of the produce as a pale straw oil

EXAMPLE 6

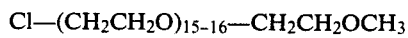

Cl—(CH$_2$CH$_2$O)$_{15-16}$—CH$_2$CH$_2$OCH$_3$

The procedure of Example 1 was repeated using

| | |
|---|---|
| Polyethylene glycol (PEG 750) monomethyl ether n = 15-16 | 100 g |
| Thionyl chloride | 60 g |
| Dimethylformamide | 0.1 g | to give the product as a yellow oil. Yield 100 g.

EXAMPLE 7

Sodium salt of 2-Hydroxy-thioxanthone

| | |
|---|---|
| 2-Mercapto-benzoic acid | 61.6 g |
| Concentrated sulfuric acid | 600 ml |
| Phenol | 188.2 g |

2-mercapto-benzoic was added to concentrated sulfuric acid and stirred until uniformly dispersed. The phenol was then added slowly and proportionwise with stirring, insuring that the temperature did not rise above 60° C. After the addition, the mixture was stirred for 1 hour at ambient temperature then for 2 hours at 95° to 100° C. The reaction mixture was permitted to cool to room temperature (usually by standing overnight) and then carefully poured into 4.5 l. of boiling water. The mixture was stirred and filtered. The filter cake was washed with water and then added to about 250 ml NaOH, and the mixture vigorously stirred. The precipitated sodium salt was filtered, washed with concentrated saline, acetone, and hexane and then oven dried, to yield 40.5 g of a bright orange solid which which could be used directly without further purifications.

EXAMPLE 8

Bis(2-oxy-thioxanthone) derivative of PEG 1000

| | |
|---|---|
| Sodium salt of 2-hydroxy-thioxanthone (from Example 7) | 26.0 g |
| Di-chloro derivative of PEG 1000 (from Example 1) | 55.2 g |
| Dimethylformamide | 100.0 g |

The reactants were added to the solvent dimethylformamide and the solution was gently boiled, allowing the solvent to strip off. The color changed from a deep red to yellow brown. The residue was cooled and diluted with 500 ml acetone. The solution was warmed to boiling treated with charcoal which was removed by filtration. The acetone was distilled off leaving 70.5 g. of the product as a viscous orange oil, which was dissolved in 155 ml water to give a 31.3% by weight of a deep orange yellow solution containing approximately 10% by weight of the active 2-oxy-thoixanthone moiety.

EXAMPLE 9

Bis(2-oxy-thioxanthone)derivative of PEG 3350

The procedure of Example 7 was repeated using:

| | |
|---|---|
| Di-chloro derivative of PEG 3350 (from Example 3) | 54.2 g |
| Sodium salt of 2-hydroxy thioxanthone (from Example 7) | 8 g |
| Dimethylformamide | 100 g |

The product was obtained as 58 g of a pale brown/orange oil which was dissolved in 11.8 ml water to give a 83.1% by weight of a visous deep orange solution containing approximately 10% by weight of the active 2-oxy-thioxanthone moiety.

EXAMPLE 10

Bis(2-oxy-thioxanthone) derivative of PEG 900

The procedure of Example 8 was repeated with the exception that 49.9 g of the dichloro derivative of PEG 900 (from Example 2) was used in place of the dichloro derivative of PEG 1000.

EXAMPLE 11

Bis(2-oxy-thioxanthone) derivative of PEG 1450

The procedure of Example 8 was repeated with the exception that 79.2 g of the dichloro derivative of PEG 1450 (from Example 4) was used in place of the dichloro derivative of PEG 1000.

EXAMPLE 12

Mono(2-oxy-thioxanthone) derivative of PEG 550 monomethyl ether

The procedure of Example 8 was repeated with the exceptions that;

(i) 30.3 g of the mono-chloro derivative of PEG 550 monomethyl ether (from Example 5) was used in place of the dichloro derivative of PEG 1000 and (ii) 13 g of the sodium salt of 2-hydroxy-thioxanthone were used.

EXAMPLE 13

Mono-(4-oxybenzophenone) derivative of PEG 750 monomethyl ether

To a solution of 2.0 g of 4-hydroxy-benzophenone in 15 ml methanol was added a solution of 0.5 g NaOH in 1.0 ml water and 6.0 ml methanol. The combined solution was refluxed for 15 minutes and then evaporated to dryness. The residue was dissolved in 10 ml dimethylformamide and 7.5 g of the mono-chloro derivative of PEG 750 monomethyl ether (from Example 6) were then added. The solution was refluxed for 1 hour, and the procedure of Example 8 was then followed to obtain 9.5 g of a yellow brown oil which was dissolved in 11.5 ml to give a 47.5% by weight of a yellow solution containing about 10% by weight of the active 4-oxybenzophenone moiety.

EXAMPLE 14

Bis(4-oxybenzophenone) derivative of PEG 1000

The procedure of Example 13 was repeated except that double the quantities of 4-hydroxy-benzophenone, NaOH, water and methanol were used and 10.1 g of the dichloro derivative of PEG 1000 (from Example 1) was used in place of the mono-chloro derivative of PEG 750 monomethyl ether to give 13.2 g of a yellow brown oil.

EXAMPLE 15

| 2 Hydroxy, 4 Methoxy benzophenone | 6.6 g |
| --- | --- |
| Water | 2.0 g |
| Methanol | 20.0 g |
| Sodium Hydroxide | 1.2 g |

The sodium hydroxide was dissolved in the water/methanol solution and the benzophenone derivative was then added and the solution was boiled gently allowing the solvent to strip off. When all of the solvent had been removed, the material was cooled and 25.0 g of DMF was added. The mixture was warmed until a solution formed, then the Dichloro Derivative of PEG 1000 (15.0 g) was added. The reaction mixture was boiled for 1 hour, allowing solvent to slowly strip off, and then cooled. The residue was dissolved in 60 ml acetone. The resulting solution was warmed and treated with charcoal which was subsequently removed by filtration, and the solvent evaporated leaving 16.5 g of dark oil which was dissolved in 33.6 ml of water to give a 33% by weight of a solution containing about 10% by weight of the active

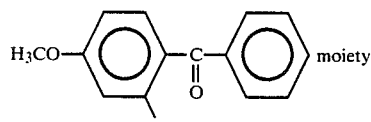 moiety

Following the procedures of Examples 13, 14 and 15 similar compounds of fluorenone, acetophenone, carbazole, propiophenone, benzaldehyde, xanthone, and anthraquinone and substituted derivatives thereof were obtained using an appropriately hydroxyl derivative of each of said compound.

The PEG derivatives of these compounds as well as those of Examples 10–12, and 14 were dissolved in a sufficient amount of water so that the solution contained about 10% by weight of the desired photoinitiator moiety. All of the PEG ethers were readily soluble in water and common organic solvents.

EXAMPLE 16

A photosensitive coating formulation was made up of the following:

| acrylamide | 7.0 g |
| --- | --- |
| methylene-bis-acrylamide (MBA) | 0.7 g |
| diethylene glycol | 2.0 g |
| bis-(oxythioxanthone derivative of PEG 1450 (10% active) (compound of Example 11) | 7.0 g |
| Triethanolamine | 1.5 g |
| 13% polyvinyl alcohol (gelvatol 20-90) | 70.8 g |
| poly(tetrafluoroethylene) powder | 9.2 g |
| Madder Lake Red | 0.5 g |

A sample of polyester mesh was coated with this formulation, and, after drying, the coated material was exposed via a photographic positive to a 2 KW mercury halide light source at a distance of 1 meter for a period of 10 secs. The resultant exposed product was developed by a cold water spray which removed the unexposed areas leaving, when dry, a negative master for screen process printing.

EXAMPLE 17

Repeated Example 16 using a formulation containing:

| Acrylamide | 3.0 g |
| --- | --- |
| methylene-bis-acrylamide | 2.0 g |
| PEG 200 di-acrylate | 1.0 g |
| bis-(4-methoxy-2-oxy-benzophenone derivative of PEG 1000 (10% active) | 5.0 g |
| Triethanolamine | 1.5 g |
| 13% polyvinyl alcohol (gelvatol 20-90) | 70.8 g |
| poly(tetrafluoroethylene)powder | 9.2 g |
| Airflex 400 | 20.0 g |
| Madder Lake Red | 0.5 g |

Following the procedure of Example 16 photopolymerizable composition containing other polymerizable materials, e.g. Vinnapas EP 14 or Vinnapas EP 11, which are also vinyl acetate ethylene copolymer emulsions place of Airflex 400 could be used with the same results. Other photoinitiators of this invention, e.g.
bis(2-oxy-thioxanthone) derivative of PEG 1000,
bis(2-oxy-thioxanthone) derivative of PEG 3350,
bis(2-oxy-thioxanthone) derivative of PEG 1450,
mono-(4-oxybenzophenone) derivative of PEG 750 monomethyl ether, mono-(2-oxy-thioxanthone) derivative of PEG 550 mono methyl ether, and bis(4-oxybenzophenone) derivative of PEG 1000 werre used in similar polymerizable systems and found to be effective. No problems were encountered in respect to inactivity or incompatibility when these novel photoiniators were used.

I claim:

1. A water-soluble photoinitiator of the formula

G—O—(CH$_2$ CH$_2$ O)$_n$—CH$_2$ CH$_2$—O—Q wherein:
G is a photoinitiator moiety selected from the group consisting of benzophenone, thioxanthenone and substituted derivatives of benzophenone and thioxanthenone, where the substituent is selected from the group consisting of alkyl, alkoxy, alkylthio, halogeno, nitro, amino, alkylamino, dialkylamino, alkanoyl, alkanoylamino, benzoylamino, and sulfonamido, wherein the alkyl group in the alkyl per se or in alkoxy, alkylthio, alkylamino, dialkylamino, alkanoyl, or alkanoylamino contains from 1 to 4 carbon atoms and may be straight chained or branched,
n has a value of at least 10, and
Q is G or a lower alkyl having from 1 to 4 carbon atoms, with the proviso that when Q is G, n has a value of at least 19.

2. A water-soluble photoinitiator according to claim 1 where Q is G.

3. A water-soluble photoinitiator according to claim 1 wherein n is an integer having a value from about 19 to about 75.

4. A water soluble photoinitiator according to claim 3 wherein G is benzophenone.

5. A water-soluble photoinitiator according to claim 3 wherein G is a compound of the formula

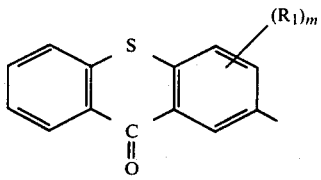

wherein $R_1$ is alkyl, alkoxy, alkylthio, halogeno, nitro, amino, alkylamino, dialkylamino, alkanoyl, alkanoylamino, benzoylamino, or sulfonamido, wherein the alkyl group in alkyl per se or in alkoxy, alkylthio, alkylamino, dialkylamino, alkanoyl, or alkanoylamino contains from 1 to 4 carbon atoms and may be straight chained or branched, and m is an integer from 0 to 2.

6. A water-soluble photoinitiator according to claim 5 wherein m is 0 and G is

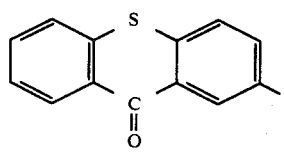

7. A water-soluble photoinitiator according to claim 6 of the formula

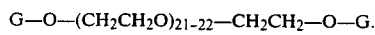

8. A water-soluble photoinitiator according to claim 6 of the formula

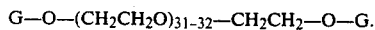

9. A water-soluble photoinitiator according to claim 6 of the formula

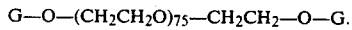

10. A water-soluble photoinitiator according to claim 6 of the formula

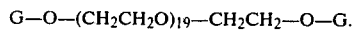

11. A water-soluble photoinitiator according to claim 6 of the formula

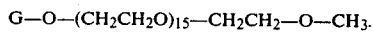

12. A water-soluble photoinitiator according to claim 4 wherein P is

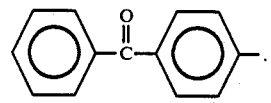

13. A water-soluble photoinitiator according to claim 12 of the formula

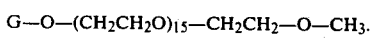

14. A water-soluble photoinitiator according to claim 12 of the formula

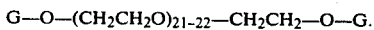

15. A water-soluble photoinitiator according to claim 4 wherein G is

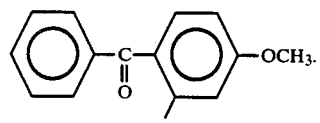

16. A water-soluble photoinitiator according to claim 15 of the formula

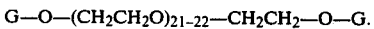

* * * * *